United States Patent [19]

Hall et al.

[11] Patent Number: 4,525,304

[45] Date of Patent: Jun. 25, 1985

[54] PROCESS FOR PREPARING OXAZOLINOAZETIDINONES

[75] Inventors: David A. Hall; Wayne A. Spitzer, both of Indianapolis, Ind.

[73] Assignee: Eli Lilly and Company, Indianapolis, Ind.

[21] Appl. No.: 442,052

[22] Filed: Nov. 16, 1982

[51] Int. Cl.³ .................. C07D 498/04; C07D 205/08
[52] U.S. Cl. ................................. 260/245.4; 204/78; 260/239 A
[58] Field of Search ...................................... 260/245.4

[56] References Cited

U.S. PATENT DOCUMENTS 4,243,588  1/1981  Spitzer et al. ...................... 260/245.4
4,271,295  6/1981  Tsuji et al. ........................... 544/182

OTHER PUBLICATIONS

Spitzer et al, J. Organic Chem. 46, 3568(1981).

Primary Examiner—Mark L. Berch
Attorney, Agent, or Firm—William C. Martens; Arthur R. Whale

[57] ABSTRACT

Compounds of the formula

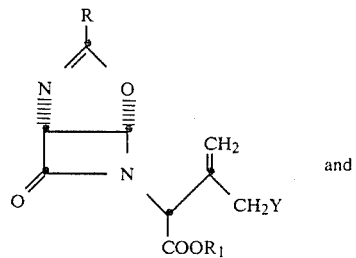

and

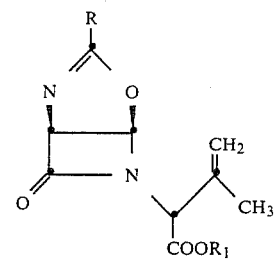

in which Y is hydrogen or hydroxyl, useful as intermediates in the production of antibiotics, are prepared by reacting a sulfinic acid of the formula

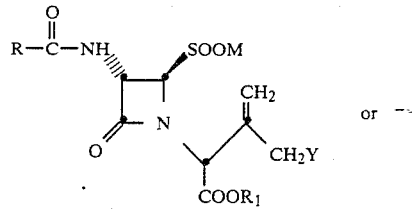

or

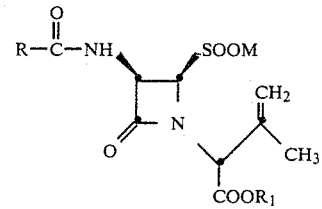

with an oxidizing agent.

16 Claims, No Drawings

PROCESS FOR PREPARING OXAZOLINOAZETIDINONES

BACKGROUND AND SUMMARY OF THE INVENTION

Over recent years, research in the synthesis of a wide range of structurally diverse β-lactam antibiotics has substantially intensified. Much emphasis has centered upon the preparation of novel bicyclic β-lactam antibiotics that differ from naturally occurring penicillins and cephalosporins not only in the structure of the C-6 or C-7 side chain or, in the case of cephalosporins, in the C-3 group, but also in the identity of the ring heteroatom (i.e., oxygen, nitrogen, or carbon in place of sulfur). In the continuing search for such novel β-lactam antibiotics, researchers have prepared a wide range of mono- and bicyclic β-lactam intermediates.

The instant invention is directed to a process for preparing β-lactam-containing bicyclic compounds useful as intermediates to β-lactam antibiotics. More particularly, the instant invention is directed to a process for preparing compounds of the formulae

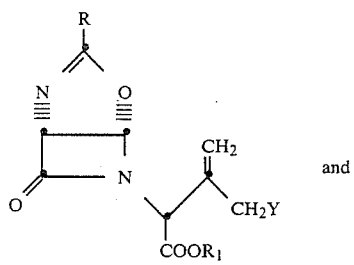

and

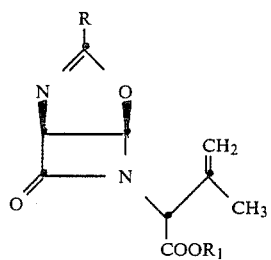

in which Y is hydrogen or hydroxyl, which comprises reacting a sulfinic acid of the formula

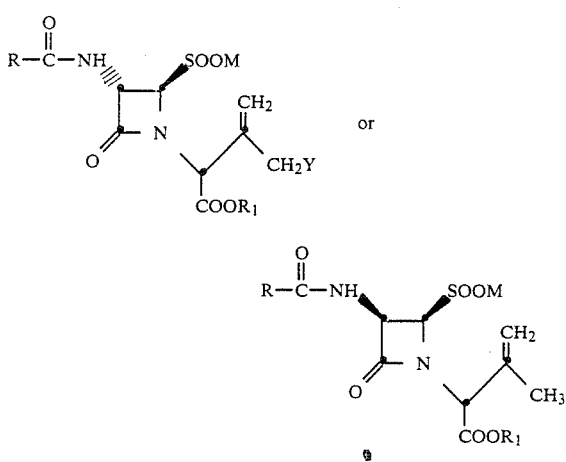

with an oxidizing agent; in which, in the above formulae,

M is hydrogen, lithium, potassium, sodium, ammonium, or substituted ammonium;

$R_1$ is hydrogen, lithium, potassium, sodium, ammonium, substituted ammonium, or a carboxylic acid protecting group; and R is (a) $C_1$ to $C_7$ alkyl, $C_3$ to $C_7$ alkenyl, halomethyl, 4-carboxybutyl, 3-formylpropyl, 4-protected carboxybutyl, or 4-protected amino-4-protected carboxybutyl;

(b) a group $R_2$ in which $R_2$ is 1,4-cyclohexadienyl, phenyl, or phenyl substituted on its ring by 1 or 2 groups selected from the group consisting of chloro, bromo, hydroxy, protected hydroxy, trifluoromethyl, $C_1$ to $C_4$ alkyl, $C_1$ to $C_4$ alkoxy, carboxy, carboxymethyl, hydroxymethyl, aminomethyl, and protected aminomethyl;

(c) a group of the formula $$R_2-(O)_m-CH_2-$$

in which $R_2$ is as defined above and m is zero or one;

(d) a group of the formula

in which $R_3$ is $R_2$ as defined above, 2-thienyl, or 3-thienyl; and W is hydroxy, protected hydroxy, carboxy, protected carboxy, amino, or protected amino; or (e) a group of the formula $$R_4-CH_2-$$

in which $R_4$ is 2-thienyl, 3-thienyl, 2-furyl, 3-furyl, 2-thiazolyl, 5-tetrazolyl, or 1-tetrazolyl.

DETAILED DESCRIPTION OF THE INVENTION

As delineated above, this invention is directed to a process for preparing oxazolinoazetidinones useful as intermediates in the preparation of β-lactam antibiotics.

The group

as used herein defines the amide function of the azetidinone sulfinic acids used as starting materials in the process of this invention. As used herein in defining the group R, the term "$C_1$ to $C_7$ alkyl" refers, for example, to methyl, ethyl, n-propyl, n-butyl, isobutyl, pentyl, n-hexyl, n-heptyl, cyclohexyl, and like aliphatic hydrocarbon chains. "$C_3$ to $C_7$ alkenyl" refers to the unsaturated hydrocarbon chains such as allyl, butenyl, pentenyl, hexenyl, heptenyl, and the like. "Halomethyl" refers, for example, to chloromethyl, bromomethyl, and the like.

The term "substituted phenyl", in defining the group R, refers to a mono- or di-substituted halophenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3-chloro-4-bromophenyl, 2-fluorophenyl and the like; a mono- or dihydroxyphenyl group such as 4-hydroxyphenyl, 3-hydroxyphenyl, 2,4-dihydroxyphenyl and the like; a mono- or di-protected hydroxyphenyl group such as 4-protected hydroxyphenyl, 3-protected hydroxyphenyl, 2,4-di-protected hydroxyphenyl and the like; a mono- or di-substituted lower alkylphenyl group such as 4-methylphenyl, 2,4-dimethylphenyl, 2-methylphenyl, 4-isopropylphenyl, 4-ethylphenyl, 3-n-propylphenyl and the like; a mono- or di-substituted lower alkoxyphenyl group for example, 2,6-dimethoxyphenyl, 4-methoxyphenyl, 3-ethoxyphenyl, 4-isopropoxyphenyl, 4-t-butoxyphenyl, 3-ethoxy-4-methoxyphenyl; a mono- or di-substituted trifluoromethylphenyl group such as 4-trifluoromethylphenyl, 3,4-di-(trifluoromethyl)phenyl, and the like; a mono- or di-substituted carboxyphenyl group, such as 4-carboxyphenyl, 2-carboxyphenyl, 3-carboxyphenyl, 2,4-dicarboxyphenyl, and the like; a phenyl ring substituted by 1 or 2 carboxymethyl groups, such as 2-carboxymethylphenyl, 3-carboxymethylphenyl, 4-carboxymethylphenyl, 2,3-dicarboxymethylphenyl, and the like; a phenyl moiety that is mono- or di-substituted by hydroxymethyl, for example, 2-(hydroxymethyl)phenyl, 4-(hydroxymethyl)phenyl, 3-(hydroxymethyl)phenyl, 3,4-di(hydroxymethyl)phenyl, and the like; phenyl groups mono- or di-substituted by aminomethyl groups, e.g. 2-(aminomethyl)phenyl, 4-(aminomethyl)phenyl, 2,3-di(aminomethyl)phenyl, and the like. The term "substituted phenyl" also represents di-substituted phenyl groups in which the substituents can be different, for example, 3-methyl-4-hydroxyphenyl, 3-chloro-4-hydroxyphenyl, 2-methoxy-4-bromophenyl, 4-ethyl-2-hydroxyphenyl, 2-hydroxy-4-chlorophenyl, 3-trifluoromethyl-4-hydroxyphenyl, 2-carboxy-4-ethoxyphenyl, 2-(aminomethyl)-4-(hydroxymethyl)phenyl, 4-carboxymethyl-2-methylphenyl, 3-(hydroxymethyl)-4-chlorophenyl, and like di-substituted phenyl groups carrying different substituents.

Illustrative R groups of the formula $R_2-(O)_m-CH_2-$ in which m is zero are 2-(cyclohexa-1,4-dien-1-yl)methyl, benzyl, 4-chlorobenzyl, 3-hydroxybenzyl, 4-hydroxy-3-methylbenzyl, 4-hydroxybenzyl, 4-bromobenzyl, 4-ethoxybenzyl, 3,4-dimethoxybenzyl, and the like. Representative groups, when m is 1, are phenoxymethyl, 3-hydroxyphenoxymethyl, 4-hydroxyphenoxymethyl, 4-chlorophenoxymethyl, 3,4-dichlorophenoxymethyl, 2-chlorophenoxymethyl, 4-methoxyphenoxymethyl, 2-ethoxyphenoxymethyl, 3,4-dimethylphenoxymethyl, 4-isopropylphenoxymethyl, 4-methyl-2-carboxyphenoxymethyl, 4-aminomethylphenoxymethyl, 4-carboxyphenoxymethyl, 4-carboxymethylphenoxymethyl, 3-trifluoromethylphenoxymethyl, 2-hydroxymethylphenoxymethyl, 2-aminophenoxymethyl, and like groups.

Illustrative of substituted arylalkyl R groups of the formula

in which $R_3$ is the same as $R_2$ defined above or 2-thienyl or 3-thienyl, are the hydroxy substituted arylalkyl groups such as the α-hydroxybenzyl or α-(protected hydroxy)benzyl group of the formula

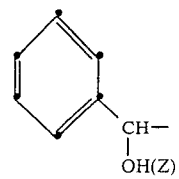

in which Z represents a hydroxy protecting group, and similar such groups in which the phenyl ring is substituted, for example, α-hydroxy-4-methoxybenzyl, α-hydroxy-3-chloro-4-hydroxybenzyl, α-hydroxy-4-hydroxybenzyl, α-hydroxy-3-bromobenzyl, α-hydroxy-3,5-dichloro-4-hydroxybenzyl, α-hydroxy-3-chloro-4-methoxybenzyl, α-hydroxy-3-chlorobenzyl, and like groups.

Also representative of the R group of the formula

are the α-carboxybenzyl or the α-(protected carboxy)-benzyl groups of the formula

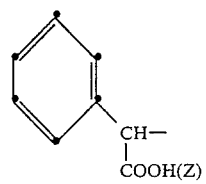

in which Z is a carboxy protecting group, and similar groups in which the phenyl ring is substituted, for example, α-(protected carboxy)-benzyl, α-(t-butoxycarbonyl)-benzyl, α-benzyloxycarbonyl-4-chlorobenzyl, α-carboxy-4-methoxybenzyl, α-carboxy-4-hydroxybenzyl, and the like.

Also representative of the R group of the formula

are the α-aminobenzyl or the α-(protected amino)-benzyl groups of the formula

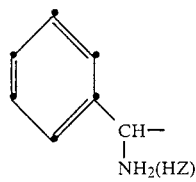

in which Z is an amino protecting group, and similar groups in which the phenyl ring is substituted, for example, α-aminobenzyl, α-amino-4-chlorobenzyl, α-amino-4-hydroxybenzyl, and the like; and also groups such as α-amino-(2-thienyl)methyl, α-amino-(2-furyl)methyl, α-amino-(1,4-cyclohexadien-1-yl)methyl, and the like.

Preferably, the group R is phenyl, 2-thienyl, 4-methylphenyl (p-toluyl), benzyl, phenoxymethyl, or 4-protected amino-4-protected carboxybutyl.

$R_1$ herein denotes, among others, hydrogen or a carboxylic acid protecting group. In addition, certain of the groups defined by R herein may include a "protected carboxy" function. The terms "protected carboxy" and "carboxylic acid protecting group", when employed herein, refer to a carboxyl group which has been protected by one of the commonly used carboxylic acid protecting groups employed to block or protect the carboxylic acid functionality of a compound while a reaction or sequence of reactions involving other functional sites of the compound are carried out. Such carboxylic acid protecting groups are noted for their ease of cleavage to the corresponding carboxylic acid by hydrolytic or by hydrogenolytic methods. Examples of carboxylic acid protecting groups include methyl, t-butyl, benzyl, 4-methoxybenzyl, $C_2$–$C_6$ alkanoyloxymethyl, 2-iodoethyl, 4-nitrobenzyl, diphenylmethyl (benzhydryl), phenacyl, p-halophenacyl, dimethylallyl, 2,2,2-trichloroethyl, tri($C_1$–$C_3$ alkyl)silyl, succinimidomethyl and like ester-forming moieties.

In addition to protection of carboxyl groups by ester formation, carboxyls can also be protected as the mixed anhydride, such as that formed with acetyl chloride, propionyl chloride, isobutyryl chloride and like acid chlorides in the presence of a tertiary amine base. Other known carboxylic acid protecting groups such as those described by E. Haslam in *Protective Groups in Organic Chemistry*, J. F. W. McOmie, Ed., Plenum Press, New York, 1973, Chapter 5, are suitable. The ester-forming protecting groups are preferred. The nature of such ester-forming groups is not critical.

Specific illustrations of the preferred carboxylic acid protecting groups for use in the process of this invention include, for example, methyl, ethyl, n-propyl, isopropyl, n-butyl, sec-butyl, isobutyl, t-butyl, 2,2,2-trichloroethyl, 2,2,2-tribromoethyl, 2-iodoethyl, benzyl, p-nitrobenzyl, succinimidomethyl, phthalimidomethyl, p-methoxybenzyl, benzhydryl, acetoxymethyl, pivaloyloxymethyl, propionoxymethyl, phenacyl, p-chlorophenacyl, p-bromophenacyl, and the like.

Highly preferred carboxylic acid protecting groups are benzyl, p-nitrobenzyl, p-methoxybenzyl, benzhydryl, and 2,2,2-trichloroethyl.

The term "protected hydroxy", when employed herein, refers to readily cleavable groups formed by reaction with an hydroxyl group. These include, for example, formyloxy, chloroacetoxy, benzyloxy, benzhydryloxy, trityloxy, 4-nitrobenzyloxy, trimethylsilyloxy, phenacyloxy, t-butoxy, methoxymethoxy, tetrahydropyranyloxy, and the like. Other typical hydroxy protecting groups, including those described by C. B. Reese in *Protecting Groups in Organic Chemistry*, supra, Chapter 3, are included within the meaning of the term "protected hydroxy" as used herein.

The term "protected amino", when employed herein, refers to readily cleavable groups formed by reaction with an amino group. These include, for example, benzyloxycarbonyl, 4-methoxybenzyloxycarbonyl, 4-nitrobenzyloxycarbonyl, 2,2,2-trichloroethoxycarbonyl, 2,4-dichlorobenzyloxycarbonyl, 2-haloethoxycarbonyl, and the like.

In the foregoing definitions, hydroxyl, carboxyl, and amino protecting groups are not exhaustively defined. The function of such groups, if necessary or desirable, is to protect reactive functional groups during synthesis. Subsequently, they are removed without disrupting the remainder of the molecule. Many protecting groups are known in the art; therefore, other protecting groups not specifically disclosed herein can be used.

The term "substituted ammonium" refers to tetramethylammonium, tetraethylammonium, tetrabutylammonium, tributylammonium, trimethylammonium, triethylammonium, tribenzylammonium, trihexylammonium, trimethylphenylammonium and triphenylammonium.

The oxazolinoazetidinones in which Y is hydrogen produced by the process of this invention are prepared from azetidinone sulfinic acids depicted by the formulas I or II following

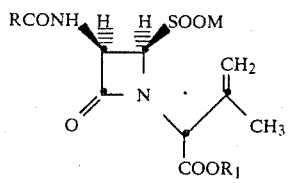

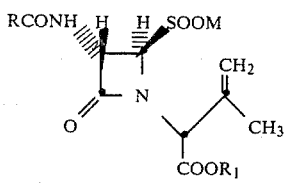

in which R and $R_1$ are as herein defined. These azetidinone sulfinic acid starting materials are prepared from their corresponding sulfinyl chlorides which, in turn, are produced from corresponding penicillin sulfoxides having, respectively, either a natural or an epi configuration. These methods are described in U.S. Pat. Nos. 4,159,266 and 4,165,315.

The oxazolinoazetidinones in which Y is hydroxyl are prepared in accordance with the process of this invention from azetidinone sulfinic acids of the formula III

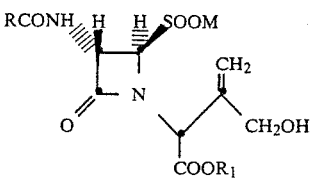

in which R and $R_1$ are as herein defined.

These azetidinone sulfinic acid starting materials in turn are available by electrolytic reduction of a cephalosporin sulfone of the formula

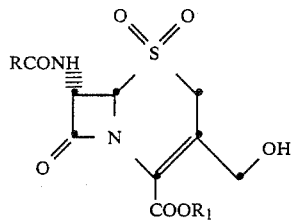

The epimeric sulfone (IV) electrolytic reduction is carried out at a potential above the reduction potential required for the cleavage of the sulfone to $C_2$ bond of the cephalosporin sulfone starting material.

The reduction further is carried out in a liquid medium stable under the conditions of electrolysis and comprised of a polar organic solvent, water, or a mixture of the two. When the medium contains a polar organic solvent, a proton source comprised of a carboxylic acid having a pKa between about zero to about five is present in an amount equal to at least one molar equivalent per molar equivalent of the cephalosporin sulfone. When the medium is water and lacks a polar organic solvent, the pH of such medium is between about 3 to about 9. The electrolysis is conducted in the presence of an electrolyte selected from the group consisting of an alkali metal salt, ammonium salts, and substituted ammonium salts, and at a temperature above the freezing point of the liquid medium and up to about 40° C.

The above electrolytic reduction is more fully described and claimed in U.S. application Ser. No. 442,075 filed this even date, now U.S. Pat. No. 4,436,596.

The epimeric sulfone (IV) can be obtained from a corresponding 3-acetoxymethyl cephalosporin by a reaction sequence involving oxidation, epimerization, and deacetylation.

Oxidation of the 3-acetoxymethyl cephalosporin to the cephalosporin sulfone is best carried out in an aqueous reaction medium maintained at a pH between about 5.0 and about 6.0 with an excess of potassium hydrogen persulfate. The oxidation proceeds well at temperatures between about 15° C. to about 45° C. The sulfone is recovered from the aqueous reaction medium by acidifying the mixture to form the free sulfone carboxylic acid and extraction of the latter with a suitable water immiscible solvent such as ethyl acetate. This process is more thoroughly described in copending application Ser. No. 442,079, filed this even date.

Epimerization of the sulfone free acid is preferably carried in an aqueous medium as follows. A slurry of the sulfone free acid in water is treated with an aqueous solution of sodium acetate containing at least an equimolar amount of sodium acetate. An aqueous solution of piperazine is then added dropwise until the pH of the solution is between about 9.5 to about 10. After the pH is adjusted, the epimerization mixture is stirred for about 5 to 15 minutes. Ethyl acetate is added to the mixture which is then acidified to a pH of about 2.0 with concentrated hydrochloric acid. The epimeric sulfone free acid is then extracted with ethyl acetate. This process is more fully described in copending U.S. application Ser. No. 442,077 filed this even date, now U.S. Pat. No. 4,477,660.

The epimerization product, the 7-(S)-acylamino cephalosporanic acid sulfone, is then deacylated with acetyl esterase to provide the 7-(S)-acylamino-3-hydroxymethyl cephalosporin sulfone.

The deacylation is preferably carried out with the esterase immobilized on a modified silica gel. This modified silica gel is prepared using silica gel of 70–230 mesh and 62–200μ particle size (i.e. Fractosil 200), E. Merck and Co.). The silica gel is prepared by first deaerating a slurry of the silica in aqueous 10% nitric acid, heating the acidic slurry for 3 hours at about 80° C. and then rinsing with water. The clean silica gel was then slurried in 10% 3-aminopropyltriethoxysilane and the slurry deaerated under vacuum. The pH is adjusted to between 3 and 4 with dilute hydrochloric acid and the slurry agitated periodically with heating at 80° C. for 3 hours. This modified silica is collected by filtration, washed with water, and dried for 16 hours at 105° C. The dried modified silica is slurried with an aqueous 3% solution of glutaraldehyde buffered by pH 7 phosphate (5–10 vol/wt of silica). The slurry is periodically agitated during 3 hours and is then washed with water and pH 7 citrate buffer.

A neutral aqueous solution of the acetyl esterase is added to the aldehyde-silica and allowed to interact for about 20 hours. The silica-enzyme complex is then transferred to a glass column and washed with pH 7 citric acid buffer.

The sulfone is dissolved in 0.2M aqueous sodium citrate, and the pH of the solution is adjusted to 7 with 1M sodium hydroxide. The solution is then passed over the silica-enzyme column. Ethyl acetate is added to the effluent and the mixture is chilled to 0° C. The pH of the cold mixture is adjusted to 2.5 with hydrochloric acid and the ethyl acetate layer is separated. The acidified aqueous phase is extracted further with ethyl acetate and all extracts are combined and washed with acidified brine and dried.

The resultant 7-(S)-acylamino-3-hydroxymethyl-3-cephem-4-carboxylic acid sulfone is recovered from the ethyl acetate by evaporation.

The deacylated sulfone may also be recovered as the carboxylic acid salt by adding sodium 2-ethylhexanoate to the combined ethyl acetate extracts or alternatively changing solvents from ethyl acetate to methanol and adding sodium acetate. As another alternative, washed and dried extract is concentrated in vacuo and the concentrate of the 3-hydroxymethyl sulfone is esterified. For example, the concentrate can be treated with diphenyldiazomethane to form diphenylmethyl 7-(S)-acylamino-3-hydroxymethyl-3-cephem-4-carboxylate sulfone.

Preferably, the esterification of the 3-hydroxymethyl sulfone acid is carried out by adding ethyl acetate containing a stoichiometric amount of diphenyldiazomethane to the effluent of the column. The 3-hydroxymethylsulfone benzhydryl ester is recovered rather than first recovering the free acid and then esterifying. This preferred route of esterification diminishes the amount of lactone formed with the 3-hydroxymethyl group and the free carboxy group by intramolecular esterification. This deacetylation process using an immobilized enzyme is further described in copending U.S. application Ser. No. 442,078, filed this even date, now U.S. Pat. No. 4,474,879.

Examples of azetidinone sulfinic acids used as starting materials in the process of this invention are:

N-(benzhydryl 3'-hydroxymethyl-2'-yl-2'-(R,S)-but-3'-enoate)-2-(R)-(ammonium sulfinate)-3-(S)-(p-toluylamido)-4-oxo-azetidine;

N-(benzhydryl 3'-hydroxymethyl-2'-yl-2'-(R,S)-but-3'-enoate)-2'-(R)-(lithium sulfinate)-3-(S)-(p-toluylamido)-4-oxo-azetidine;

N-(lithium 3'-hydroxymethyl-2'-yl-2'-(R,S)-but-3'-enoate)-2'-(R)-(lithium sulfinate)-3-(S)-(p-toluylamido)-4-oxo-azetidine;

N-(lithium 3'-hydroxymethyl-2'-yl-2'-(R,S)-but-3'-enoate)-2'-(R)-(lithium sulfinate)-3-(S)-(phenoxyacetamido)-4-oxo-azetidine;

N-(benzhydryl 3'-hydroxymethyl-2'-yl-2'-(R,S)-but-3'-enoate)-2'-(R)-(ammonium sulfinate)-3-(S)-(phenoxyacetamido)-4-oxo-azetidine;

N-(benzhydryl 3'-hydroxymethyl-2'-yl-2'-(R,S)-but-3'-enoate)-2'-(R)-(lithium sulfinate)-3-(S)-(phenylacetamido)-4-oxo-azetidine;

N-(benzhydryl 3'-hydroxymethyl-2'-yl-2'-(R,S)-but-3'-enoate)-2'-(R)-(ammonium sulfinate)-3-(S)-(phenylacetamido)-4-oxo-azetidine;

N-(t-butyl 3'-hydroxymethyl-2'-yl-2'-(R,S)-but-3'-enoate)-2'-(R)-(sodium sulfinate)-3-(S)-(phenylacetamido)-4-oxo-azetidine;

N-(benzhydryl 3'-hydroxymethyl-2'-yl-2'-(R,S)-but-3'-enoate)-2'-(R)-(ammonium sulfinate)-3-(S)-2-(thien-2-yl)acetamido-4-oxo-azetidine;

N-(4-methoxybenzyl) 3'-hydroxymethyl-2'-yl-2'-(R,S)-but-3'-enoate)-[2'-(R)-(lithium sulfinate)-3-(S)-[2-(thien-2-yl)acetamido-4-oxo-azetidine;

N-(benzhydryl 3'-hydroxymethyl-2'-yl-2'-(R,S)-but-3'-enoate)-2'-(R)-(sodium sulfinate)-3-(S)-2-(fur-2-yl)acetamido-4-oxo-azetidine;

N-(t-butyl 3'-hydroxymethyl-2'-yl-2'-(R,S)-but-3'-enoate)-2'-(R)-(tetraethylammonium sulfinate-3-(S)-[2-(tetrazol-1-yl)acetamido]-4-oxo-azetidine;

N-(benzhydryl 3'-hydroxymethyl-2'-yl-2'-(R,S)-but-3'-enoate)-2'-(R)-(sodium sulfinate)-3-(S)-(2-amino-2-phenylacetamido)-4-oxo-azetidine;

N-(tetramethylammonium 3'-hydroxymethyl-2'-yl-2'-(R,S)-but-3'-enoate)-2'-(R)-(tetramethylammonium sulfinate)-3-(S)-[2-amino-2-(4-hydroxyphenyl)acetamido]-4-oxo-azetidine;

N-(triphenylammonium 3'-hydroxymethyl-2'-yl-2'-(R,S)-but-3'-enoate)-2'-(R)-(triphenylammonium sulfinate)-3-(S)-[2-hydroxy-2-(3-chlorophenyl)acetamido]-4-oxo-azetidine;

N-(benzhydryl 3'-hydroxymethyl-2'-yl-2'-(R,S)-but-3'-enoate)-2-(R)-(potassium sulfinate)-3-(S)-[2-hydroxy-2-(4-hydroxyphenyl)acetamido]-4-oxoazetidine;

N-(benzhydryl 3'-hydroxymethyl-2'-yl-2'-(R,S)-but-3'-enoate)-2-(R)-(ammonium sulfinate)-3-(S)-[D-(5-(2,4-dichlorobenzyloxycarbonylamino)-5-(benzhydrylcarboxylate)valeramido-4-oxo-azetidine;

N-[(4-methoxybenzyl) 3'-hydroxymethyl-2'-yl-2'-(R,S)-but-3'-enoate]-2-(R)-(tetraethylammonium sulfinate)-3-(S)-[D-(5-amino)-5-(4-methoxybenzyl)-carboxylate)valeramido)-4-oxo-azetidine;

N-(benzhydryl 3'-hydroxymethyl-2'-yl-2'-(R,S)-but-3'-enoic-ester)-2'-(R)-(tetraethylammonium sulfinate)-3-(S)-[D-(5-(2,4-dichlorobenzyloxycarbonyl))-5-(benzhydryl carboxylate)valeramido]-4-oxo-azetidine;

N-[(4-methoxybenzyl) 3'-hydroxymethyl-2'-yl-2'-(R,S)-but-3'-enoate]-2-(R)-(sodium sulfinate)-3-(S)-[D-(5-(2,4-dichlorobenzyloxycarbonylamino))-5-((4-methoxybenzyl)carboxylate)valeramido]-4-oxo-azetidine;

N-(benzhydryl 3'-hydroxymethyl-2'-yl-2'-(R,S)-but-3'-enoate)-2-(R)-(sodium sulfinate)-3-(S)-[D-(5-benzyloxycarbonylamino)-5-(benzhydryl carboxylate)valeramido]-4-oxo-azetidine;

N-(4-methoxybenzyl) 3'-hydroxymethyl-2'-yl-2'-(R,S)-but-3'-enoate]-2-(R)-(sodium sulfinate)-3-(S)-[D-(5-(4-methoxybenzyloxycarbonylamino))-5-((4-methoxybenzyl)carboxylate)valeramido]-4-oxo-azetidine;

N-(benzhydryl 3'-hydroxymethyl-2'-yl-2'-(R,S)-but-3'-enoate)-2-(R)-(potassium sulfinate)-3-(S)-[D-(5-(2,4-dichlorobenzyloxycarbonylamino))-5-(benzhydryl carboxylate)valeramido]-4-oxo-azetidine;

N-(t-butyl 3'-hydroxymethyl-2'-yl-2'-(R,S)-but-3'-enate)-2-(R)-(sodium sulfinate)-3-(S)-[D-(5-(2,4-dichlorobenzyloxycarbonylamino))-5-((t-butyl)-carboxylate)valeramido]-4-oxo-azetidine;

N-(t-butyl 3'-hydroxymethyl-2'-yl-2'-(R,S)-but-3'-enoate)-2-(R)-(potassium sulfinate)-3-[D-(5-((4-methoxybenzyloxycarbonyl)amino)-5-((t-butyl)-carboxylate)valeramido]-4-oxo-azetidine;

N-(t-butyl 3'-hydroxymethyl-2'-yl-2'-(R,S)-but-3'-enoate)-2-(R)-(sodium sulfinate)-3-(S)-(p-toluylamido)-4-oxo-azetidine;

N-[(4-methoxybenzyl) 3'-hydroxymethyl-2'-yl-'-(R,S)-but-3'-enoate]-2-(R)-(sodium sulfinate)-3-(S)-(p-toluylamido)-4-oxo-azetidine;

N-(benzhydryl 3'-hydroxymethyl-2'-yl-2'-(R,S)-but-3'-enoate)-2-(R)-(potassium sulfinate)-3-(S)-(p-toluylamido)-4-oxo-azetidine;

N-(potassium 3'-hydroxymethyl-2'-yl-2'-(R,S)-but-3'-enoate)-2-(R)-(potassium sulfinate)-3-(S)-(p-toluylamido)-4-oxo-azetidine;

N-(potassium 3'-hydroxy-2'-yl-2'-(R,S)-but-3'-enoate)-2-(R)-(potassium sulfinate)-3-(S)-(2-phenoxyacetamido)-4-oxo-azetidine;

N-(t-butyl 3'-hydroxymethyl-2'-2'-(R,S)-but-3'-enoate)-2-(R)-(sodium sulfinate)-3-(S)-(2-phenoxyacetamido)-4-oxo-azetidine;

N-[(4-methoxybenzyl) 3'-hydroxymethyl-2'-yl-2'-(R,S)-but-3'-enoate]-2-(R)-(sodium sulfinate)-3-(S)-(phenoxyacetamido)-4-oxo-azetidine;

N-[(4-methoxybenzyl) 3'-hydroxymethyl-2'-yl-2'-(R,S)-but-3'-enoate]-2-(R)-(sodium sulfinate)-3-(S)-(2-phenylacetamido)-4-oxo-azetidine;

N-(benzhydryl 3'-hydroxymethyl-2'-yl-2'-(R,S)-but-3'-enoate)-2-(R)-(potassium sulfinate)-3-(S)-(phenylacetamido)-4-oxo-azetidine;

N-(t-butyl 3'-hydroxymethyl-2'-yl-2'-(R,S)-but-3'-enoate)-2-(R)-(sodium sulfinate)-3-(S)-[2-(thien-2-yl)acetamido]-4-oxo-azetidine;

N-(benzhydryl 3'-hydroxymethyl-2'-yl-2'-(R,S)-but-3'-enoate)-2-(R)-(potassium sulfinate)-3-(S)-[2-(thien-2-yl)acetamido]-4-oxo-azetidine;

N-[(4-methoxybenzyl) 3'-hydroxymethyl-2'-yl-2'-(R,S)-but-3'-enoate]-2-(R)-(sodium sulfinate)-3-(S)-[2-(thien-2-yl)acetamido]-4-oxo-azetidine;

N-(benzhydryl 3'-hydroxymethyl-2'-yl-2'-(R,S)-but-3'-enoate)-2-(R)-(tri-n-butylammonium sulfinate)-3-(S)-(p-toluylamido)-4-oxo-azetidine;

N-(benzhydryl 3'-hydroxymethyl-2'-yl-2'-(R,S)-but-3'-enoate)-2-(R)-(sodium sulfinate)-3-(S)-[2-(thien-2-yl)acetamido]-4-oxo-azetidine;

N-(benzhydryl 3'-hydroxymethyl-2'-yl-2'-(R,S)-but-3'-enoate)-2-(R)-(sodium sulfinate)-3-(S)-[2-(phenoxyacetamido)]-4-oxo-azetidine;

N-(benzhydryl 3'-hydroxymethyl-2'-yl-2'-(R,S)-but-3'-enoate)-2-(R)-(sodium sulfinate)-3-(S)-(2-phenylacetamido)-4-oxo-azetidine;

N-(benzhydryl 3'-hydroxymethyl-2'-yl-2'-(R,S)-but-3'-enoate)-2-(R)-(sodium sulfinate)-3-(S)-[D-(5-(2,4-dichlorobenzoxycarbonylamino))-5-(benzylhydryl carboxylate)valeramido]-4-oxo-azetidine;

N-(benzhydryl 3'-hydroxymethyl-2'-yl-2'-(R,S)-but-3'-enoate)-2-(R)-(sodium sulfinate)-3-(S)-(p-toluylamido)-4-oxo-azetidine;

N-(sodium 3'-hydroxymethyl-2'-yl-2'-(R,S)-but-3'-enoate)-2-(R)-(sodium sulfinate)-3-(S)-(2-phenoxyacetamido)-4-oxo-azetidine;

N-(3'-hydroxymethyl-2'-yl-2'-(R,S)-but-3'-enoic acid)-2-(R)-(sulfinic acid)-3-(S)-(p-toluylamido)-4-oxo-azetidine; and the like.

The conversion of azetidinone sulfinic acids to oxazolinoazetidinones in accordance with the process of this invention involves their treatment with an oxidizing agent.

The reaction of the azetidinone sulfinic acid with the oxidizing agent generally is carried out by mixing at least about 1 mole and up to about 1.5 moles of the oxidizing agent with each mole of the azetidinone sulfinic acid. An even larger excess of the oxidizing agent can be employed; however, no advantage is gained thereby. Preferably, therefore, the ratio of reactants is from about 1.0 to about 1.1 moles of oxidizing agent per mole of the azetidinone sulfinic acid. The resulting mixture, generally dissolved in water, a suitable inert organic solvent, or a mixture of water and a water-miscible inert organic solvent, is maintained at the reaction temperature, a temperature generally from about 0° C. to about 30° C., for a period sufficient for completion of the reaction.

By the term "inert organic solvent" is meant an organic solvent which, under the conditions of oxazolinoazetidinone formation, does not appreciably react either with the reactants or with the products. Suitable inert organic solvents include, for example, aromatic hydrocarbons, such as benzene, toluene, ethylbenzene, cumene, and the like; halogenated hydrocarbons, such as carbon tetrachloride, chlorobenzene, bromoform, bromobenzene, methylene chloride, ethylene dichloride, 1,1,2-trichloroethane, ethylene dibromide, and the like; amides, such as N,N-dimethylformamide, and the like; alcohols, such as methanol, ethanol, and the like; esters, such as ethyl acetate, and the like; nitriles, such as acetonitrile, and the like; and any other appropriate inert solvents. Preferred solvents include N,N-dimethylformamide, acetonitrile, ethyl acetate, methylene chloride, and other like solvents.

The oxidizing agent employed in the process of this invention can be any of a wide range of such agents. Typical agents include, for example, $Pb^{+4}$ compounds, such as lead tetraacetate, lead oxide, and the like; $Mn^{+4}$ compounds, such as manganese acetoacetonate, manganese oxide, and the like; sodium hypochlorite; N-haloimides, such as N-bromosuccinimide, and the like; ammonium cerium nitrate; and other like compounds. Preferably, the oxidizing agent is a $Pb^{+4}$ compound, in particular, lead tetraacetate, or an N-bromoimide, in particular, N-bromosuccinimide.

The temperature of the reaction defined by the process of this invention generally is from about 0° C. to about 30° C. Preferably, the reaction temperature is at the lower end of this range, generally from about 0° C. to about 5° C.

Typically, the oxidation reaction herein defined is complete in a very short time, generally in a matter of a few minutes. However, the time of reaction can be greatly extended, for example, to several hours, without detrimental effect. Normally the time of reaction will be no longer than about one hour.

The oxazolinoazetidinones produced according to the process of this invention can be recovered and purified using routine techniques recognized in the art, including, for example, extraction, various forms of chromatographic purification, lyophilization, and the like.

As noted above, the oxazolinoazetidinones produced by the process of this invention are useful as intermediates in the production of antibiotically active compounds.

Oxazolinoazetidinones of formula V

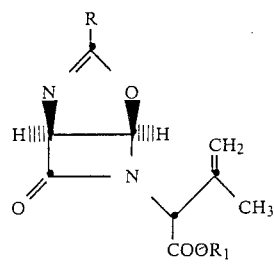

prepared using azetidinone sulfinic acids of formula I herein, are useful in the preparation of oxygen analogues of penicillins as described in U.S. Pat. No. 4,243,588.

Oxazolinoazetidinones of formula VI

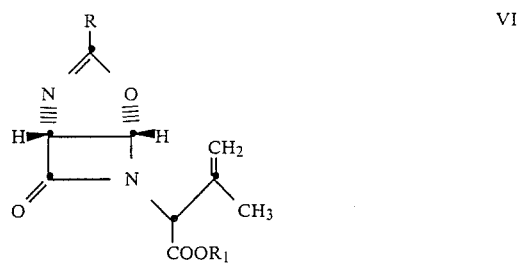

prepared using azetidinone sulfinic acids of formula II herein, are useful in the preparation of oxygen analogues of cephalosporins as described in U.S. Pat. Nos. 4,220,766, 4,271,295, and 4,271,296. In accordance with the teaching of these patents, the oxazolinoazetidinones are used in an involved reaction sequence. They are first treated with base to produce the corresponding conjugated double bond compound. The conjugated product then is treated with propargyl alcohol, hydrated, cleaved at the side chain with ozone, reduced, substituted with halogen, treated with triphenylphosphine to form a Wittig reagent, and recyclized to give antibacterial 1-oxadethiacephalosporins.

Oxazolinoazetidinones of formula VII

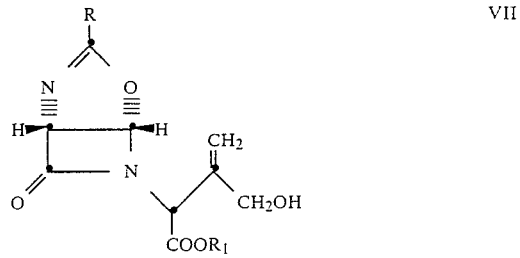

prepared using azetidinone sulfinic acids of formula III herein, are useful in the preparation of oxygen analogues of cephalosporins as described in U.S. Pat. Nos. 4,220,766, 4,271,295, and 4,271,296. In accordance with the teaching of these patents, the oxazolinoazetidinones are treated with boron trifluoride etherate to produce the corresponding 3-exomethylene oxygen analogue cephalosporin. The latter can be converted to the 3-methyl-3-cephem compound using triethylamine.

Examples of oxazolinoazetidinones which can be produced by the process of this invention are:

benzhydryl (2'(R,S))-2'-[(1R,5S)-3-[D-(4-protected amino-4-protected carboxybutyl)]-7-oxo-4-oxa-2,6-diazabicyclo[3.2.0]hept-2-en-6-yl]-4'-hydroxy-3'-exomethylene butyrate;

benzyl (2'(R,S))-2'-[(1R,5S)-3-(D-phenoxymethyl)-7-oxo-4-oxa-2,6-diazabicyclo[3.2.0]hept-2-en-6-yl]-4'-hydroxy-3'-exomethylene butyrate;

p-nitrobenzyl (2'(R,S))-2'-[(1R,5S)-3-(D-benzyl)-7-oxo-4-oxa-2,6-diazabicyclo[3.2.0]hept-2-en-6-yl]-4'-hydroxy-3'-exomethylene butyrate;

p-methoxybenzyl (2'(R,S))-2'-[(1R,5S)-3-[D-(4-(benzyloxycarbonylamino))-4-(p-methoxybenzylcarboxylate)-but-1-yl]-7-oxo-4-oxa-2,6-diazabicyclo[3.2.0]hept-2-en-6-yl]-4'-hydroxy-3'-exomethylene butyrate;

2,2,2-trichloroethyl (2'(R,S))-2'-[(1R,5S)-3-(D-phenyl)-7-oxo-4-oxa-2,6-diazabicyclo[3.2.0]hept-2-en-6-yl]-4'-hydroxy-3'-exomethylene butyrate;

benzhydryl (2'(R,S))-2'-[(1R,5S)-3-(D-p-tolyl)-7-oxo-4-oxa-2,6-diazabicyclo[3.2.0]hept-2-en-6-yl]-4'-hydroxy-3'-exomethylene butyrate;

p-nitrobenzyl (2'(R,S))-2'-[(1R5S)-3-(D-phenoxymethyl)-7-oxo-4-oxa-2,6-diazabicyclo[3.2.0]hept-2-en-6-yl]-4'-hydroxy-3'-exomethylene butyrate; and the like.

The following examples are provided to illustrate the process of this invention. They are not intended to be limiting upon the scope thereof.

EXAMPLE 1

Benzhydryl (2'-(R,S))-2'-[(1R,5S)-3-[D-(4-(2,4-dichlorobenzoxycarbonylamino))-4-(benzhydryl carboxylate)-but-1-yl]-7-oxo-4-oxa-2,6-diazabicyclo[3.2.0-]hept-2-en-6-yl]-4'-hydroxy-3'-exomethylene butyrate.

Procedure A a. Electrolysis

A solution of methanol (48.0 ml) and acetic acid (3.0 ml) was made 0.1M in sodium acetate and then benzhydryl 7-(S)-[D-(5-(2,4-dichlorobenzoxycarbonylamino))-5-(benzhydryl carboxylate)valeramido]-3-hydroxymethyl-3-cephem-4-carboxylate sulfone (4.0 g) was added. The solution was then added to the cathode compartment of an electrolytic cell, thermostated at 0° C., containing a lead plate cathode and a platinum anode separated by a cation exchange membrane. The electrolysis was conducted at a constant current of 400 ma (19 ma/cm²) until HPLC analysis of the catholyte showed the electrolysis to be complete with production of N-[benzhydryl 3'-hydroxymethyl-2'-yl-2'-(R,S)-but-3'-enoate]-2-(R)-(sodium sulfinate)3-(S)-[D-((5-(-2,4-dichlorobenzoxycarbonylamino))-5-(benzhydryl carboxylate))valeramido]-4-oxo-azetidine.

b. NBS Oxidation

The catholyte was transferred to a flask and chilled to approximately 0° C. in an alcohol/ice bath. A methanol solution (50 ml) of N-bromosuccinimide (1.18 g) was slowly added to the cold catholyte with constant stirring. At the end of the addition HPLC of the resultant solution showed the oxidation to be complete. To this solution containing the oxazoline azetidinone product was added an aqueous solution of 1:1 0.3M phosphate solution at pH 7: saturated sodium chloride solution containing 1% sodium hydrogen sulfite. This buffered solution was then extracted twice with ethyl acetate, the two ethyl acetate layers were combined and washed again with the above 1:1 0.3M phosphate solution/saturated sodium chloride solution, dried over magnesium sulfate, filtered, and the solvent removed in vacuo to yield foam. A preparative thin layer chromatograph (using a 3:2 v:v ethyl acetate:toluene eluant) of a small amount of this foam yielded benzhydryl (2'-(R))-2'-[(1R,5S)-3-[D-(4-(2,4-dichlorobenzyloxycarbonylamino))-4-(benzhydryl carboxylate)-but-1-yl]-7-oxo-4-oxa-2,6-diazabicyclo[3.2.0]hept-2-en-6-yl]-4'-hydroxy-3'-exomethylene butyrate and the corresponding 2'-(S) isomer. n.m.r: (CDCl₃) C-2'-(S)-isomer: δ0.8 to 2.6 (m, 6, -(C$\underline{H}$₂)₃)-, 4.04 (ab quartet, 2,

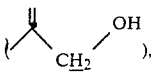

4.96 (m, 1, 4-methine proton of butyl group), 4.96 (s, 1, C-2'H), 5.03, 5.28 (2×(s, 1, exomethylene proton)), 5.06 (d, 1, C-1H), 6.10 (d, 2, C-5H), 6.89, 6.92 (2×(s, 1, benzhydryl group methine protons), 7 to 7.8 (m, 24, aromatic protons and amido proton); C-2'-(R)-isomer. δ0.8 to 2.6 (m, 6, -(C$\underline{H}$₂)₃-), 4.2 (ab quartet, 2,

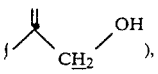

4.9 (m, 1, 4-methine proton of butyl group), 4.95 (s, 1, C-2'H), 5.01 (d, 1, C-1 H), 5.1, 5.37 (2×(s, 1, exomethylene proton)), 5.75 (d, 1, C-5 H), 6.87, 6.91 (2×(s, 1, benzhydryl group methine proton), 7 to 7.8 (m, 24, aromatic and amido group protons).

Procedure B a. Electrolysis A solution of acetonitrile (25.5 ml), water (8.5 ml) and acetic acid (2 ml) was made 0.1M in tetraethylammonium perchlorate. Benzhydryl 7-(S)-[D-(5-(2,4-dichlorobenzoxycarbonylamino))-5-(benzhydryl carboxylate)valeramido]-3-hydroxymethyl-3-cephem-4-carboxylate sulfone (1 g) was added to this solution. This solution was in turn added to the cathode compartment of an electrolytic cell thermostatted at 0° C. The anolyte, a 1.0M tetraethylammonium acetate buffer (pH 3.6), was added to the anode compartment, and the catholyte was deoxygenated by a stream of argon. The electrolysis was carried out by applying a potential of −1.50V to the cathode, and maintaining this potential until the current had diminished to zero. HPLC analysis of the cathode solution demonstrated that the starting material had all been consumed with production of N-[benzhydryl 3'-hydroxymethyl-2'-yl-2'-(R,S)-but-3'-enoate]-2-(R)-(sodium sulfinate)-3-(S)-[D-((5-(-2,4-dichlorobenzoxycarbonylamino))-5-(benzhydryl carboxylate))valeramido]-4-oxo-azetidine.

b. Lead tetraacetate oxidation

The catholyte solution was then removed from the cathode compartment, and chilled ethyl acetate (90 ml) was added. The layers were separated, and the ethyl acetate layer was washed with chilled 0.3M phosphate buffer (40 ml, 3×) and with saturated sodium chloride solution (40 ml, 1×). The ethyl acetate solution was dried over sodium sulfate, filtered, and a small volume (8 ml) was removed for n.m.r. analysis. The volume of the remaining solution was reduced to approximately 25 ml. This solution was chilled and lead tetraacetate (1 mM) was added while stirring, followed by the addition of another portion (88 mg) of lead tetraacetate. When HPLC analysis of the reaction mixture indicated the reaction to be complete, the precipitate was removed by vacuum filtration and the ethyl acetate filtrate was washed with 1:1 saturated sodium chloride: 0.3M pH 7 phosphate buffer solution (25 ml, 2×), dried over sodium sulfate, filtered and evaporated to dryness under vacuum to yield 557 mg of foam. A small portion of this material (40 mg) was subjected to HPLC on a Water's Associates $C_{18}$ preparatory column using 30% water in acetonitrile as the eluant. Benzhydryl (2'-(S))-2'-[(1R,5S)-3-(D-(4-(2,4-dichlorobenzyloxycarbonylamino))-4-(benzhydryl carboxylate)-but-1-yl-7-oxo-4-oxa-2,6-diazabicyclo[3.2.0]hept-2-en-6-yl]-4'-hydroxy-3'-exomethylenebutyrate (14 mg) was recovered. The n.m.r. (CDCl$_3$) of this compound showed a doublet at δ6.1 with a coupling constant of 3.2 Hz, indicating that the compound was the 2'-(S) isomer.

EXAMPLE 2

Benzhydryl (2'-(R,S))-2'-[(1R,5S)-3-(p-toluyl)-7-oxo-4-oxa-2,6-diazabicyclo[3.2.0]hept-2-en-6-yl]-4'-hydroxy-3'-exomethylenebutyrate.

Procedure A

A. Electrolysis

A solution of methanol (34 ml) and acetic acid (2.0 ml) was made 0.5M in sodium perchlorate. Benzhydryl 7-(S)-(p-toluylamido)-3-hydroxymethyl-3-cephem-4-carboxylate (4.0 g) was added to this solution and the resultant mixture was added to the cathode compartment of an electrolytic cell thermostatted at 0° C. The catholyte was deoxyenated with a small stream of argon. The electrolysis was begun at a cathodic current of 750 ma (37.5 ma/cm$^2$) and gradually stepped down to 50 ma over a 3000 second time period. At the end of this time period, HPLC analysis of the catholyte indicated that the reduction was very near completion with production of N-[benzhydryl-3'-hydroxymethyl-2'-yl-2'-(R,S)-but-3'-enoate]-2-(R)-(sodium sulfinate)-3-(S)-(p-toluylamido)-4-oxoazetidine. The electrolysis was stopped.

B. NBS Oxidation

The catholyte was then transferred to a flask and chilled to 0° C. in an alcohol/ice bath. A methanol solution (50 ml) of N-bromosuccinimide (1.96 g) was then added to the chilled catholyte over a ten minute period, at the end of which time period HPLC analysis of the resultant reaction mixture indicated that the oxidation was complete. A 1:1 0.3M pH 7 phosphate:-saturated sodium chloride solution that was 1% in sodium hydrogen sulfite was added to the reaction mixture, and the resultant solution was extracted twice with ethyl acetate. The ethyl acetate layers were combined, washed three times with the above 1% sodium hydrogen sulfite solution, dried over magnesium sulfate, filtered and evaporated to dryness in vacuo, to yield a white foam. This white foam contained crude benzhydryl (2'-(R,S))-2'-[(1R,5S)3-(p-toluyl)-7-oxo-4-oxa-2,6-diazobicyclo[3.2.0]hept-2-en-6-yl]-4'-hydroxy-3'-exomethylene butyrate (3.32 g, 94% crude yield). This crude product mixture was recrystallized from 1:3 hexanes/toluene (15 ml) to yield 2.03 g of a mixture of the 2'-(R) and 2'-(S) isomers. N.M.R. analysis of the crude product mixture showed that the 2'R and 2'S isomers were present in approximately equal amounts and that 5 to 10% of the crude product mixture was the lactone of the following structure.

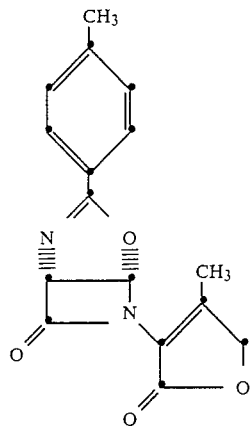

The amounts of each compound present were determined by the ratio of the areas under the peaks for the C-5 proton of each molecule. Similarly, n.m.r. analysis of the recrystallized product mixture shows that only the 2'-(R) and 2'-(S) isomers (no lactone) are present in equal amounts. The n.m.r. of the crude product mixture and recrystallized product mixture showed the chemical shifts of the characteristic C-5 protons of the above molecules to be as follows: n.m.r. (DMSOd$_6$) 2'-(R) isomer, δ 6.10; 2'-(S) isomer, δ 6.28; lactone, δ 6.65.

Procedure B

A. Electrolysis

A solution of methanol (48 ml) and acetic acid (3.0 ml) was made 0.5M in sodium perchlorate. Benzhydryl 7-(S)-(p-toluylamido)-3-hydroxymethyl-3-cephem-4-carboxylate (3.0 g) was added to this solution and the resultant mixture was added to the cathode compartment of an electrolytic cell containing a zinc cathode (24 cm$^2$) and thermostatted at 0° C. The electrolysis was conducted at a cathodic current of 21 ma/cm$^2$ with production of N-[benzhydryl-3'-hydroxymethyl-2'-yl-2'-(R,S)-but-3'-enoate]-2-(R)-(sodium sulfinate)-3-(S)-(p-toluylamido)4-oxo-azetidine.

B. NBS Oxidation

Upon completion of the electrolysis, the catholyte was transferred to a flask and chilled to 0° C. in an alcohol/ice bath. A methanol solution (50 ml) of N-bromosuccinimide (1.47 g) was added to the chilled catholyte slowly through a dropping funnel, and at the end of the addition HPLC analysis of the resultant reaction mixture indicated that the oxidation was complete. A 1:1 0.3M pH 7 phosphate:saturated sodium chloride solution that was 1% in sodium hydrogen sulfite was added to the reaction mixture, and the resultant solution was extracted twice with ethyl acetate. The ethyl acetate layers were combined, washed three times with a 1:1 0.3M pH 7 phosphate:saturated sodium chloride solution, dried over magnesium sulfate, filtered, concentrated and placed in a refrigerator. The chilled concentrate was filtered to yield 1.477 g of crystals of the title product. n.m.r. (major identifying peaks only) (DMSOd$_6$): δ 6.18 (d, 1, C-5 proton of 2'-(R) isomer), 6.38 (d, 1, C-5 proton of 2 '-(S) isomer.

Procedure C

A. Electrolysis

A solution of methanol (48 ml) and acetic acid (4 ml) was made 0.1M in sodium acetate. Benzhydryl 7-(S)-(p- toluylamido)-3-hydroxymethyl-3-cephem-4-carboxylate (4.0 g) to this solution and the resultant mixture was added to the cathode compartment of an electrolyte cell containing a lead plate cathode (24 cm$^2$) and thermostatted at 0° C. The electrolysis was conducted at 25 ma/cm$^2$ for approximately 3500 seconds with production of N-[benzhydryl-3'-hydroxymethyl-2'-yl-2'-(R,S)-but-3'-enoate]-2-(R)(sodium sulfinate)-3-(S)-(p-toluylamido)-4-oxoazetidine.

B. NBS Oxidation

When the electrolysis was completed, the catholyte was transferred to a flask and chilled to 0° C. in an ice/alcohol bath. A methanol solution (approximately 50 ml) of N-bromosuccinimide (1.5 equivalents) was added to the chilled catholyte slowly through a dropping funnel. When the HPLC analysis of the solution indicated that the oxidation reaction was complete, a 1:1 0.3M pH 7 phosphate:saturated sodium chloride solution that was 1% in sodium hydrogen sulfite was added to the reaction mixture, and the resultant solution was extracted with ethyl acetate (2×). The ethyl acetate layers were combined, washed with 1:1 0.3M pH 7 phosphate:saturated sodium chloride solution (3×), dried over magnesium sulfate, filtered, concentrated and placed in the refrigerator. The chilled solution was filtered to collect crystals (2.57 g) of the title product. n.m.r. (major identifying peaks only) (DMSOd$_6$): δ 6.18 (d, 1, C-5 proton of 2'-(R) isomer), 6.38 (d, 1, C-5 proton of 2'-(S) isomer).

EXAMPLE 3

Benzhydryl (2'-(R,S))-2'-[(1R,5S)-3-(2-(thien-2-yl))-7-oxo-4-oxa-2,6-diazabicyclo[3.2.0]hept-2-en-6-yl]-4'-hydroxy-3'-exomethylene butyrate.

A. Electrolysis

A solution of 10% water in DMF (35 ml) and acetic acid (2.0 ml) was made 0.1N in tetraethylammonium perchlorate. Benzhydryl 7α-[2-(thien-2-yl)acetamido]-3-hydroxymethyl-3-cephem-4-carboxylate (2.0 g) was added to this solution, and the resultant mixture was added to the cathode compartment of an electrolytic cell thermostatted at 0° C. An anode compartment containing a cation exchange membrane separator and a platinum anode in a pH 3.6 1N acetate buffer was then placed in the cathode compartment of the electrolytic cell. The catholyte was de-oxygenated with a small stream of argon. The electrolysis was done by adjusting the cathodic current to 150 ma (10.7 ma/cm$^2$) and maintaining that current throughout the electrolysis.

B. Lead Tetraacetate Oxidation

The catholyte, containing N-[benzhydryl-3'-hydroxymethyl-2'-yl-(R, S)-but-3'-enoate]-2-(R)-(tetraethylammonium sulfinate)-3-(S)-(thien-2-ylacetamido)-4-oxoazetidine, was removed from the cathode and acidic sodium chloride solution was added. The solution was extracted with ethyl acetate and the extract was washed with portions of acidic sodium chloride solution, then dried over anhydrous magnesium sulfate and filtered. The filtrate was chilled to 0° C. in an alcohol/ice bath. Lead tetraacetate (1.6 g) was added to the ethyl acetate solution and allowed to react for 15 minutes at 0° C. At the end of this time the lead tetraacetate was removed by filtration and the ethyl acetate filtrate was washed several times with a pH 7.0 0.3N phosphate solution. The ethyl acetate filtrate was then dried over magnesium sulfate, filtered and evaporated under reduced pressure to yield a light yellow foam. This foam contained predominantly the C-2'-(S) isomer of benzhydryl (2'-(R,S))-2'-[(1R,5S)-3-(2-(thien-2-yl))-7-oxo-4-oxa-2,6-diazabicyclo[3.2.0]hept-2-en-6-yl]-4'-hydroxy-3'-exomethylene butyrate. n.m.r.: (DMSOd$_6$) δ 6 6.10 (d, 1, C-5H).

EXAMPLE 4

Sodium (2'-(R,S))-2'-[(1R,5S)-3-(p-toluyl)-7-oxo-4-oxa-2,6-diazabicyclo[3.2.0]hept-2-en-6-yl]-4'-hydroxy-3'-exomethylene butyrate.

Procedure A a. Electrolysis

Sodium 7-(S)-(p-toluylamido)-3-hydroxymethyl-3-cephem-4-carboxylate (1.0 g) was dissolved in an aqueous 0.25M sodium sulfate solution. The solution was added to the cathode compartment of an electrolytic cell wherein the cell compartments were separated by a Nafion TM 427 cation exchange membrane. The anolyte was also an aqueous 0.25M sodium sulfate solution. The pH of the catholyte was set at 5.5 and maintained at that value during the electrolysis by the addition of 0.1N sulfuric acid. The cell was thermostatted at 10° C. and the potential of the cathode was maintained at −1.85 V with production of N-[sodium 3'-hydroxymethyl-2'-yl-2'-(R,S)-but-3'-enoate]-2-(R)-(sodium sulfinate)-3-(S)-(p-toluylamido)-4-oxoazetidine.

b. Oxidation

The catholyte was removed from the cathode compartment, and 1M phosphate solution (pH 7, 5 ml) and ethyl acetate (50 ml) were added to the catholyte. This solution was chilled in an ice-alcohol bath, then the pH of the solution was adjusted to 2.5 by the addition of 12N sulfuric acid. A dimethylformamide solution (2 ml) of N-bromosuccinimide (800 mg) was added dropwise to the chilled solution over approximately 5 minutes, allowing the yellow color to dissipate after each addition. During this time the pH of the cooled reaction mixture changed from 2.5 to 1.8. Sodium bisulfite (200 mg) was added and the layers were allowed to separate. The aqueous layer was extracted with ethyl acetate (50 ml), all the while maintaining the two layers at low temperature by the addition of ice. The ethyl acetate layer and extract were combined then washed with a 0.1N hydrochloric acid:saturated sodium chloride solution (50 ml, 2×). The ethyl acetate solution was then dried over magnesium sulfate and filtered. The filtrate was evaporated to the point of crystallization and then further evaporated until approximately 10 ml of filtrate remained. This solution was refrigerated overnight, yielding 406 mg (52%) of a 1:4 C-2'-(R):C-2'-(S) mixture of sodium (2'-(R,S))-2'-[(1R,5S)-3-(p-toluyl)-7-oxo-oxa-2,6-diazabicyclo[3.2.0]hept-2-en-6-yl]-4'-hydroxy-3'-exomethylene butyrate. n.m.r.: (DMSOd$_6$) C-2'-(S) isomer: 2.32 (s, 3, para-methyl 3.92 (s, 2,

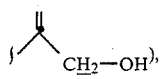

4.86 (s, 1, C-2' H), 5.14, 5.34 (2×(br. s., 1, exomethylene protons), 5.40 (d, 1, C-1 H), 6.28 (d, 1, C-5 H), 7.22–7.88 (m, 4, aromatic protons); C-2'-(R)-isomer, the same as the C-2'-(S) isomer except C-5 H absorbs at δ 6 6.05 instead of δ 6 6.28; f.d.m.s.: 316.

Procedure B a. Electrolysis

The electrolysis was run as above, with the following changes: the anolyte and catholyte were both a 0.5M aqueous sodium chloride solution. The cell compartments were separated by a microporous glass frit and the potential of the cathode was maintained at −1.85 V throughout the electrolysis. Finally, the pH of the catholyte was set at 7 and maintained between 4.5 to 7.5 by the addition of 0.1N hydrochloric acid.

b. Oxidation

The catholyte, containing N-[sodium 3'-hydroxymethyl-2-yl-2'-(R,S)-but-3'-anoate]-2-(R)-(sodium sulfinate)-3-(S)-(p-toluylamido)-4-oxoazetidine, was transferred from the cathode compartment and chilled in an ice-alcohol bath. To the chilled solution was added sodium bicarbonate (1.5 g) then a dimethylformamide solution (2 ml) of N-bromosuccinimide (399 mg). (The initial pH of the reaction mixture was 8.1, and the final pH was 7.4 and the minimum pH was 7.0). The progress of the reaction was monitored by HPLC. Approximately 0.5 hour after the first addition, a second addition of dimethylformamide solution (2 ml) of N-bromosuccinimide (289 mg) was made. Approximately 10 minutes later a third addition of N-bromosuccinimide (90 mg), dissolved in dimethylformamide, was made. Based on the HPLC analysis of the reaction mixture, 385 mg of a combination of the 2'-(R) and 2'-(S) isomers was present.

Procedure C a. Electrolysis

The electrolysis was run as in Procedure B, with the following changes: The catholyte and the anolyte were an aqueous 0.25M sodium sulfate solution. The potential of the cathode was maintained at −1.85 V throughout the electrolysis. The pH of the catholyte was maintained at 8.0 during the electrolysis by the addition of 0.1N sulfuric acid. The pH of the catholyte ranged from 5 to 8.5 during the electrolysis.

b. Oxidation

The catholyte, containing N-8 sodium 3'-hydroxymethyl-2-yl-2'-(R,S)-but-3'-anoate]-2-(R)-(sodium sulfinate)-3-(S)-(p-toluylamido)-4-oxoazetidine, was removed from the cathode compartment and layered with ethyl acetate (50 ml). The resulting mixture was chilled in an ice-alcohol bath then NBS (469 mg) was added. The pH of the reaction mixture was 6.0, and the final pH was 2.0. The layers were allowed to separate and the ethyl acetate layer was washed with chilled 0.1N hydrochloric acid-saturated sodium chloride (40 ml, 2×). The product was extracted into water by washing the ethyl acetate layer with 1:1 5% sodium bicarbonate:saturated sodium chloride solution (40 ml, then 20 ml). The aqueous extracts were combined and stored in a freezer for approximately 0.75 h. The combined aqueous extracts were then placed in an ice-alcohol bath, then ethyl acetate (30 ml) was added. The pH of the aqueous layer was adjusted to 2.5 by the addition of 12N sulfuric acid followed by the addition of 1N sulfuric acid. The acidified aqueous layer was further extracted with ethyl acetate (30 ml, 2×) the three ethyl acetate extracts were combined, dried over magnesium sulfate and filtered. The filtrate was evaporated to the point of crystallization under reduced pressure and was placed in the refrigerator overnight. The crystallized product (160 mg) was collected by filtration. The n.m.r. spectrum of the product crystals (DMSOd$_6$) showed the product to be approximately an 85:15 mixture of 2'-(S) to 2'-(R) isomer.

EXAMPLE 5 p-Nitrobenzyl 2'-(R)-2'-[(1S,5R)-3-phenoxymethyl-7-oxo-4-oxa-2,6-diazabicyclo[3.2.0]-hept-2-en-6-yl]-3'-exomethylene butyrate.

To 1.0 gram of p-nitrobenzyl 2R-(3β-phenoxyacetamido-2-oxo-4β-sulfinoazetidin-1-yl)-3-methyl-3-butenoate and 0.9 grams of lead tetraacetate in 50 ml of dimethylformamide were added 50 mg of lithium chloride. The mixture was maintained at room temperature for two hours. Ethyl acetate was added, and the resulting mixture was washed with saturated sodium chloride solution. The organic layer was separated, dried over magnesium sulfate and evaporated in vacuo to dryness with recovery of the title compound. The structure of the oxazolineazetidinone product was confirmed by treating the product with triethylamine to isomerize the β,γ double bond to α,β. The resulting isomerized product was purified by chromatography. n.m.r.: (CDCl$_3$) 1.85 (s, 3, methyl), 2.26 (s, 3, methyl), 4.67 (s, 2, -C$\underline{H}_2$-O-phenyl), 5.23 (bs, 3, -C$\underline{H}_2$ from p-nitrobenzyl and proton from β-lactam), 6.00 (d, 1, 4 Hz, proton from β-lactam), 6.60–7.65 (bm, 7, aromatic protons from phenoxy and p-nitrophenyl), 8.15 (d, 2, aromatic protons from p-nitrophenyl).

EXAMPLE 6 p-Nitrobenzyl 2'-(R)-2'-[(1R,5S)-3-phenoxymethyl-7-oxo-4-oxa-2,6-diazabicyclo[3.2.0]hept-2-en-6-yl]-3'-exomethylene butyrate.

To 10 ml of acetonitrile were added 200 mg (38 mmol) of p-nitrobenzyl 2R-(3α-phenoxyacetamido-2-oxo-4β-sulfinoazetidin-1-yl)-3-methyl-3-butenoate. To the mixture then were added 170 mg (38 mmol) of lead tetraacetate. The mixture was maintained at room temperature for about two minutes after which it was washed, first with saturated sodium chloride solution and then with saturated sodium bicarbonate solution. The mixture was dried over magnesium sulfate and evaporated in vacuo to dryness. An nmr spectrum of the product showed the presence of a doublet at 5.83 δ (3 Hz), characteristic of the oxazolinoazetidinone.

EXAMPLE 7 p-Nitrobenzyl 2'-(R)-2'-[(1R,5S)-3-phenoxymethyl-7-oxo-4-oxa-2,6-diazabicyclo[3.2.0]hept-2-en-6-yl]-3'-exomethylene butyrate.

To 5 ml of methylene chloride were added 200 mg (38 mmol) of p-nitrobenzyl 2R-(3α-phenoxyacetamido-2-oxo-4β-sulfinoazetidin-1-yl)-3-methyl-3-butenoate. To the mixture then were added 5 ml of sodium hypochlorite. The mixture was maintained at room temperature for about 5 minutes after which it was washed, first with saturated sodium chloride solution and then with saturated sodium bicarbonate solution. The mixture was dried over magnesium sulfate and evaporated in vacuo to dryness. An nmr spectrum of the product showed the presence of a doublet at 5.83 δ (3 Hz), characteristic of the oxazolinoazetidinone.

We claim:

1. A process for preparing compounds of the formula

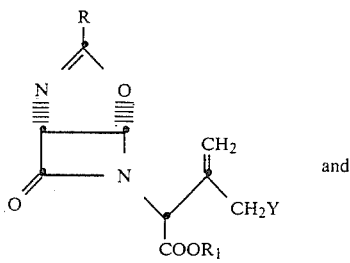

and

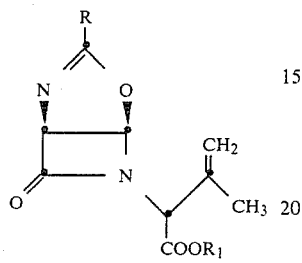

in which Y is hydrogen or hydroxyl, which comprises reacting a sulfinic acid of the formula

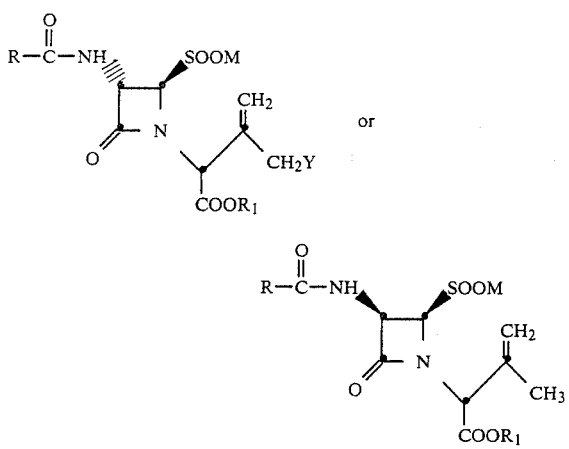

with an oxidizing agent selected from the group consisting of a $Pb^{+4}$ compound, an $Mn^{+4}$ compound; sodium hypochlorite, an N-haloimide, and ammonium cerium nitrate; in which, in the above formulae, M is hydrogen, lithium, potassium, sodium, ammonium, or substituted ammonium;

$R_1$ is hydrogen, lithium, potassium, sodium, ammonium, substituted ammonium, or a carboxylic acid protecting group; and R is (a) $C_1$ to $C_7$ alkyl, $C_3$ to $C_7$ alkenyl, halomethyl, 4-carboxybutyl, 3-formylpropyl, 4-protected carboxybutyl, or 4-protected amino-4-protected carboxybutyl;

(b) a group $R_2$ in which $R_2$ is 1,4-cyclohexadienyl, phenyl or phenyl substituted on its ring by 1 or 2 groups selected from the group consisting of chloro, bromo, hydroxy, proteced hydroxy, trifluoromethyl, $C_1$ to $C_4$ alkyl, $C_1$ to $C_4$ alkoxy, carboxy, carboxymethyl, hydroxymethyl, aminomethyl, and protected aminomethyl;

(c) a group of the formula $$R_2-(O)_m-CH_2-$$

in which $R_2$ is as defined above and m is zero or one;

(d) a group of the formula $$R_3-CH- \atop W$$

in which $R_3$ is $R_2$ as defined above, 2-thienyl, or 3-thienyl; and W is hydroxy, protected hydroxy, carboxy, protected carboxy, amino, or protected amino; or (e) a group of the formula $$R_4-CH_2-$$

in which $R_4$ is 2-thienyl, 3-thienyl, 2-furyl, 3-furyl, 2-thiazolyl, 5-tetrazolyl, or 1-tetrazolyl.

2. Process of claim 1, in which the oxidizing agent is a $Pb^{+4}$ compound

3. Process of claim 2, in which the oxidizing agent is lead tetraacetate.

4. Process of claim 1, in which the oxidizing agent is an N-bromoimide.

5. Process of claim 4, in which the oxidizing agent is N-bromosuccinimide.

6. Process of claim 1, in which the oxidation is carried out in an aqueous medium.

7. Process of claim 1, in which R is selected from the group consisting of phenyl, 2-thienylmethyl, p-toluyl, benzyl, phenoxymethyl, and 4-protected amino-4-protected carboxybutyl.

8. Process of claim 7, in which $R_1$ is selected from the group consisting of benzyl, p-nitrobenzyl, p-methoxybenzyl, benzhydryl, and 2,2,2-trichloroethyl.

9. Process of claim 7, in which R is 4-protected amino-4-protected carboxybutyl.

10. Process of claim 9, in which R is 4-(2,4-dichlorobenzyloxycarbonylamino)-4-(benzhydryl carboxylate)-but-1-yl.

11. Process of claim 10, in which $R_1$ is benzhydryl.

12. Process of claim 8, in which R is p-toluyl and $R_1$ is benzhydryl.

13. Process of claim 8, in which R is 2-thienyl and $R_1$ is benzhydryl.

14. Process of claim 7, in which R is p-toluyl and $R_1$ is sodium.

15. Process of claim 1, in which the sulfinic acid has the formula

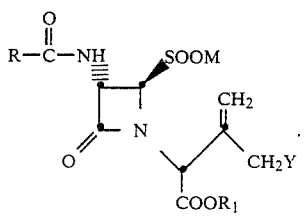

16. Process of claim 15, in which Y is hydroxyl.

* * * * *